US006627043B1

United States Patent
Mäntylä

(10) Patent No.: US 6,627,043 B1
(45) Date of Patent: Sep. 30, 2003

(54) MEASURING AMOUNT OF SILICONE COATING ON PAPER WEB

(75) Inventor: Markku Mäntylä, Kangasala (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 09/806,068

(22) PCT Filed: Oct. 5, 1999

(86) PCT No.: PCT/FI99/00824

§ 371 (c)(1),
(2), (4) Date: Mar. 23, 2001

(87) PCT Pub. No.: WO00/20842

PCT Pub. Date: Apr. 13, 2000

(30) Foreign Application Priority Data

Oct. 6, 1998 (FI) .................................................. 982171

(51) Int. Cl.[7] .......................... D21H 19/10; G01N 21/89
(52) U.S. Cl. ........................ 162/198; 162/263; 356/431; 250/339.12; 118/665
(58) Field of Search ................................ 162/198, 252, 162/253, 262, 263, 265, DIG. 6, DIG. 10; 250/330, 339.01, 339.06, 339.11, 341.8, 339.12; 118/665, 688, 689, 690; 427/9; 356/51, 431

(56) References Cited

U.S. PATENT DOCUMENTS

| | | | | |
|---|---|---|---|---|
| 3,631,526 A | | 12/1971 | Brunton | 250/339.11 |
| 3,793,524 A | * | 2/1974 | Howarth | 250/339.1 |
| 4,631,408 A | | 12/1986 | Zelmanovic et al. | 250/339.11 |
| 4,639,942 A | | 1/1987 | Puumalainen | 378/45 |
| 4,679,899 A | * | 7/1987 | Kobayashi et al. | 350/96.3 |
| 4,818,576 A | * | 4/1989 | Pennance et al. | 428/40 |
| 4,957,770 A | * | 9/1990 | Howarth | 427/9 |
| 5,795,394 A | * | 8/1998 | Belotserkovsky et al. | 118/665 |
| 6,179,918 B1 | * | 1/2001 | Belotserkovsky | 118/665 |
| 6,262,419 B1 | | 7/2001 | Huth-Fehre et al. | 250/341.8 |

FOREIGN PATENT DOCUMENTS

| | | |
|---|---|---|
| EP | 268029 | 5/1988 |
| JP | 9239914 A | 9/1997 |
| WO | WO9725605 | 7/1997 |
| WO | WO9941590 A1 | 8/1999 |

* cited by examiner

Primary Examiner—Steven P. Griffin
Assistant Examiner—Eric Hug
(74) Attorney, Agent, or Firm—Alston & Bird LLP

(57) ABSTRACT

The invention relates to a method and an apparatus for measuring the amount of silicone coating on a moving paper or board web. In the invention, the characteristics of the coating (4a) are measured by means of reflection measurement or transmission measurement. The amount of the silicone in the coating is measured by measuring an absorption peak that is characteristic of the silicone in the mid-infrared range.

13 Claims, 1 Drawing Sheet

MEASURING AMOUNT OF SILICONE COATING ON PAPER WEB

FIELD OF THE INVENTION

The invention relates to a method of measuring the amount of silicone coating on a moving paper or cardboard web, wherein the amount of the coating is measured substantially continuously.

The invention further relates to an apparatus for measuring the amount of silicone coating on a moving paper or cardboard web, the apparatus comprising a radiation source for producing a beam, means for directing the beam at a material to be measured, a detector for measuring the beam arriving from the material to be measured, and means for processing a signal from the detector, the apparatus being arranged to measure the amount of the coating, substantially continuously.

BACKGROUND OF THE INVENTION

When silicone-coated products are being manufactured, it is important to monitor the amount of the silicone coating on a moving substrate, such as a paper or cardboard web. Silicone coating is used for paper grades that require small release strength. An example is release paper for adhesive paper. The amount of the silicone coating in a particular paper grade should be kept constant. A typical amount of silicone varies from 0.5 to 1.5 g/m$^2$. Silicone is one of the most expensive materials in the manufacture of paper, and therefore measuring the amount of silicone accurately reduces costs considerably and provides products that are more uniform in quality.

The amount of a coating on a moving web can be measured, for example, with a method based on the difference between dry weights. In this method the basis weight of the web is measured by means of beta radiation absorption, and moisture is measured by infrared measurement. Both measurements are carried out before and after a coating station. The wet weight is subtracted from the basis weight to obtain the dry weight, and the difference between the dry weights determines the amount of the coating. The equipment is rather complicated and the accuracy of the final result depends on the accuracies of four meters. In practice, the accuracy of the measurement based on the difference between dry weights varies approximately from 0.5 to 1 g/m$^2$. Therefore, the arrangement is not at all suitable for measuring the amount of silicone coating, where the accuracy should be about 0.1 g/m$^2$. Also, the arrangement is expensive since it comprises four meters and two measuring frames.

The amount of the silicone coating is also measured by an X-ray fluorescence method, where the target of measurement is subjected to X-radiation radiation, fluorescence peaks caused by silicon atoms are measured, and the amount of the silicone coating is determined on the basis thereof. However, the fluorescence includes both the effect of the silicon atoms in the silicone coating and the effect of, for example, silicon atoms contained in clay used as a filler in the base paper. Therefore the measurement result is not accurate. U.S. Pat. No. 4,639,942 discloses an X-ray fluorescence method where the accuracy is improved by the geometry of the equipment and by calculation. However, the arrangement is highly complicated and rather slow due to the required calculation. Further, the use of X-radiation in the measuring apparatus is hazardous to those working near the apparatus.

The prior art also teaches measurement of the amount of the silicone coating in the near-infrared range, where a weak absorption peak can be located in the coating on a wavelength of about 2.3 micrometers. However, due to the weakness of the absorption it is difficult to achieve sufficient accuracy of measurement. Another problem is that binders, such as latex, used in the paper and the coating absorb in this range, which makes the measurement inaccurate if the effect of the interfering component is not measured before the siliconization.

EP 0,268,029 discloses a continuous method of measuring the amount of silicone coating on a moving paper web. The method comprises measuring the gloss of the web surface before and after the coating process. The difference between the measured gloss values is then used to determine the amount of the silicone coating. The arrangement requires two devices for measuring the gloss, which makes the measuring equipment cumbersome, complicated and expensive. Further, the results of gloss measurements are rather unreliable and not very accurate. Therefore, the amount of the silicone coating calculated on the basis of the gloss measurements is often erroneous and misleading.

SUMMARY OF THE INVENTION

The purpose of the present invention is to provide a method which avoids the aforementioned drawbacks.

The method according to the invention is characterized by directing an infrared beam at the moving paper or cardboard web and measuring an absorption peak that is characteristic of the silicone coating in the middle infrared range on a wavelength of from 2.5 to 5 micrometers.

Further, the apparatus according to the invention is characterized in that the radiation source produces an infrared beam, and that the apparatus is arranged to measure the amount of the silicone coating by measuring an absorption peak that is characteristic of the coating in the middle infrared range on a wavelength of from 2.5 to 5 micrometers.

The invention is based on the idea of directing an infrared beam at a moving paper or cardboard web, measuring an absorption peak that is characteristic of the silicone coating in the middle infrared range on a wavelength of 2.5 to 5 micrometers, and determining the amount of the silicone coating on the basis of the measurement. The idea of a preferred embodiment is to measure an absorption peak that is characteristic of a methyl group in the silicone coating in a wavelength range of about 3.4 micrometers.

An advantage of the invention is that the amount of the silicone coating can be measured very accurately and reliably. Measurement can be carried out by one meter and, in the case of reflection measurement, by half a measuring frame.

BRIEF DESCRIPTION OF THE DRAWINGS

The Invention will be described in greater detail in the accompanying drawings, in which.

DETAILED DESCRIPTION OF THE PREFERRED EMBODIMENTS

Figure 1:
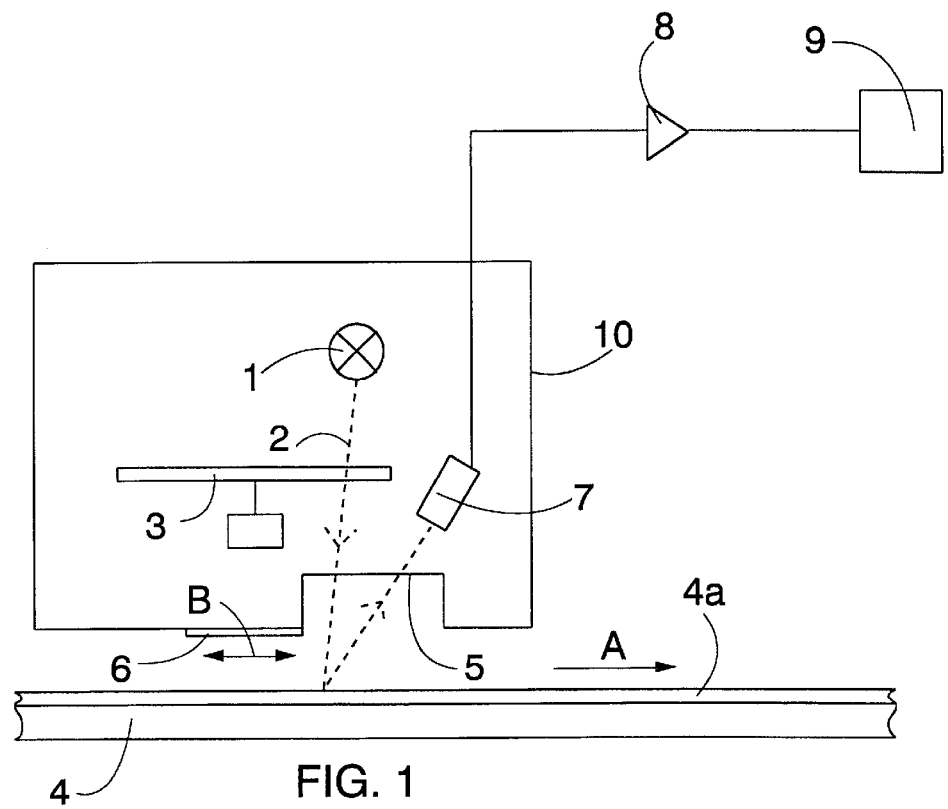
FIG. 1 shows schematically a measuring apparatus according to the invention.

FIG. 1 shows a measuring arrangement where radiation reflected from a target is measured. In other words, the source of the radiation and the receiver are on the same side of the target to be measured. This type of measurement is called reflection measurement.

FIG. 1 shows a measuring apparatus 10 comprising a radiation source 1, which produces an infrared beam 2. The radiation source 1 can be, for example, a halogen lamp or some other suitable source for producing an infrared beam. The infrared beam 2 is passed through a filter 3. The filter 3 filters light in such a way that only the light that is essential for the measurement and that is on the correct wavelength band is able to propagate all the way to the target of the measurement. The filter 3 can be, for example, a rotary filter disc comprising several interference filters, or some other filter arrangement known per se. The structure of the filter 3 is known per se to those skilled in the art, wherefore it will not be described in greater detail herein. After the filter 3 the infrared beam 2 is directed through a window 5 at a paper or cardboard web 4 moving on the paper machine. The distance between the measuring apparatus 10 and the paper or cardboard web 4 varies typically from 0 to 50 mm. The measuring apparatus 10 can be arranged to measure a moving paper or cardboard web in a continuous manner by mounting the apparatus in a measuring frame placed transversely across the web. The measuring devices measuring different paper properties are arranged to traverse the measuring frame. If the measuring frame comprises only one beam to which the measuring devices are fastened, the distance between the measuring apparatus 10 according to the invention and the paper or cardboard web 4 varies between 0 and 50 mm. On the other hand, if the measuring frame is an O frame comprising two measuring beams, one above and the other one below the paper, the distance between the measuring apparatus 10 and the paper or cardboard web 4 varies between 0 and 6 mm. The window 5 can be made of silica glass or sapphire, for example. The paper or cardboard web 4 travels in the direction of arrow A. The surface of the paper or cardboard web 4 is provided with a silicone coating 4a. Instead of a moving paper or cardboard web 4, the moving substrate which carries the coatings to be measured can also be for example a roll of a paper-coating machine, a roll of a paper machine and/or, generally, the surface of a metal sheet. The equipment may also comprise a reference sample 6, which is moved at certain intervals to the point of measurement, as shown by arrow B. The sample 6 is used as a reflection reference and the measurement result it provides indicates the condition of the radiation source 1, a detector 7 and the window 5. Reference measurement can also be used to correct the actual measurement result, if desired.

The reflected infrared beam 2 is supplied to the detector 7. The signals are supplied from the detector 7 via preamplifiers 8 to a computer 9 which processes the measured data in a manner known per se. For the sake of clarity, FIG. 1 does not show optics that is possibly required to align and direct the infrared beam 2. The light can be guided/directed by means of focusing optics, an optical fibre or an optical fibre bundle, for example.

The amount of the silicone coating 4a is measured substantially continuously during the papermaking process. This means that the measurement is an on-line measurement of the papermaking process. Naturally, even if the measurement were interrupted for a rather short period due to calibration or some other reason, it is still considered to be continuous.

In the silicone used as a coating, a silicon atom is surrounded by methyl groups that bond together. The silicone coating thus contains methyl groups ($CH_3$).

Figure 2:
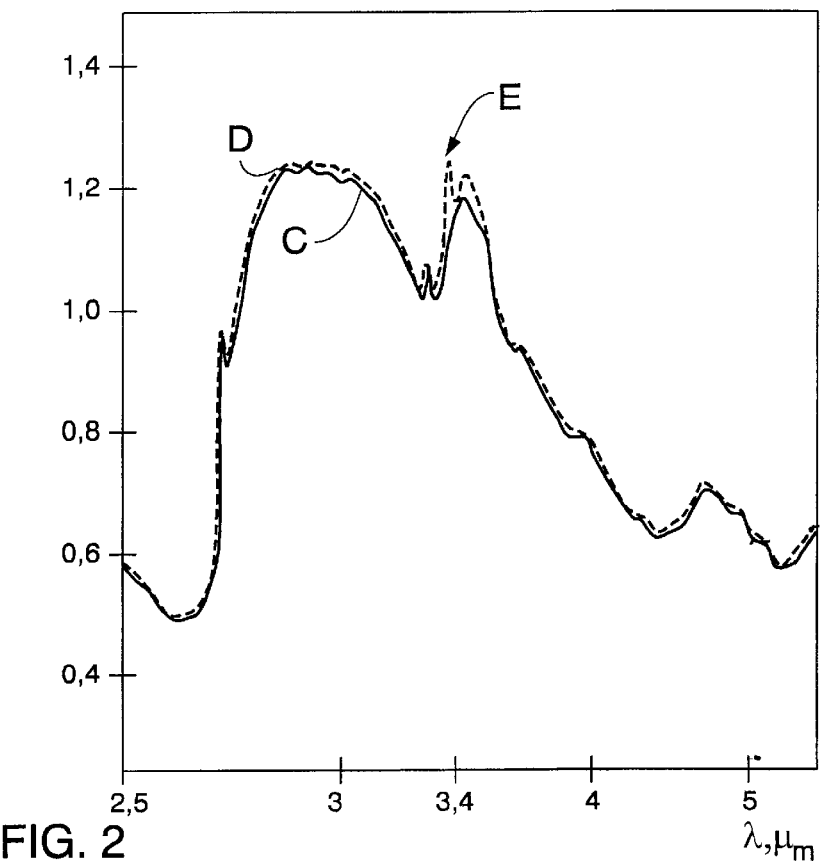
FIG. 2 shows spectra of base paper and silicone-coated paper.

In FIG. 2, curve C shows the reflection spectrum of base paper, and curve D, which is denoted by a broken line, shows the reflection spectrum of silicone-coated paper. The horizontal axis shows the wavelength $\lambda$ in micrometers, and the vertical axis shows the absorbency. When the spectra were measured, an absorption peak E was found in the silicone-coated paper on a wavelength of 3.4 micrometers. This absorption peak is characteristic of the methyl group ($CH_3$) of the silicone coating 4a and it can be found in the coating. However, such a methyl group formed around silicon cannot be found in the base paper, wherefore the measurement result is specifically proportional to the amount of the silicone coating. Thus, silicon atoms that possibly exist in the base paper do not affect the accuracy of the measurement. The response on the wavelength of 3.4 micrometers is rather significant, which facilitates the measurement. Furthermore, the aforementioned wavelength range does not really exhibit any absorption bands, resulting from other materials used in the papermaking, that would interfere with the measurement of the silicone coating. By arranging the apparatus of FIG. 1 to measure an absorption peak on a wavelength of about 3.4 micrometers, it is possible to measure the amount of the silicone coating.

Reference wavelengths suitable for measuring the amount of the silicone coating include 3.3 and 3.7 micrometers or some other suitable reference wavelength which does not absorb the methyl group ($CH_3$). The wavelength of 3.7 micrometers is particularly advantageous since it can also be used as a reference in measuring the amount of water. The amount of water is preferably measured on a wavelength of about 3.175 micrometers, for example.

The drawing and the related description are only intended to illustrate the inventive idea. The details of the invention may vary within the scope of the claims. Therefore the invention can be applied not only in reflection measurement but also in transmission measurement.

What is claimed is:

1. A method for measuring the amount of silicone coating on a moving paper or cardboard web during a papermaking process, comprising:
   directing a beam of infrared light at the moving web;
   receiving light emanating from the moving web; and
   analyzing the received light so as to measure an absorption peak that is characteristic of the silicone coating in the mid-infrared range at a wavelength of from 2.5 to 5 micrometers, wherein the amount of silicone coating is measured by measuring an absorption peak that is characteristic of a methyl group in the silicone coating.

2. The method according to claim 1, wherein the absorption peak of the silicone coating is measured at a wavelength of about 3.4 micrometers.

3. The method according to claim 1, wherein the steps of directing the light onto the web and receiving the light emanating from the web are performed by a measuring apparatus arranged at a distance of less than 50 millimeters from the web.

4. The method according to claim 3, wherein the measuring apparatus is disposed at a distance of less than 6 millimeters from the substrate.

5. A method for measuring the amount of silicone coating on a moving substrate, comprising:
   directing a beam of infrared light at the moving substrate;
   receiving light emanating from the moving substrate; and
   analyzing the received light so as to measure an absorption peak that is characteristic of the silicone coating in the mid-infrared range at a wavelength of from 2.5 to 5 micrometers, wherein the received light is analyzed so as to measure a reference value for the measurement of the absorption peak of the silicone coating at a wavelength of about 3.7 micrometers.

6. A method for measuring the amount of silicone coating on a moving substrate, comprising:

directing a beam of infrared light at the moving substrate;

receiving light emanating from the moving substrate; and analyzing the received light so as to measure an absorption peak that is characteristic of the silicone coating in the mid-infrared range at a wavelength of from 2.5 to 5 micrometers, wherein the substrate contains water, and further comprising simultaneously measuring the amount of water in the substrate at a wavelength of about 3.175 micrometers.

7. The method according to claim 6, further comprising measuring a reference value for the measurement of the amount of water at a wavelength of about 3.7 micrometers.

8. An apparatus for measuring the amount of a silicone coating on at moving substrate, comprising:

a radiation source operable to produce infrared radiation and direct a beam of said radiation onto the moving substrate;

a detector configured to detect an absorption peak of the silicone coating at a wavelength of about 3.4 micrometers, the detector being further configured to receive the beam after the beam has impinged oil on the moving substrate and to produce a signal in response thereto, the signal being indicative of the absorption peak of the silicone coating; and a processor connected to the detector and operable to process the signal therefrom so as to substantially continuously measure the amount of silicone coating on the moving substrate.

9. The apparatus of claim 8, wherein the substrate contains water and the detector and processor are further structured and arranged to simultaneously measure the amount of water in the moving substrate at a wavelength of about 3.175 micrometers.

10. An apparatus for measuring the amount of a silicone coating on a moving paper or cardboard web during a papermaking process, comprising:

a radiation source operable to produce infrared radiation and direct a beam of said radiation onto the moving web;

a detector configured to detect an absorption peak characteristic of a methyl group in the silicone coating in the mid-infrared range at a wavelength of between about 2.5 micrometers and about 5 micrometers, the detector being further configured to receive the beam after the beam has impinged on the moving web and to produce a signal in response thereto, the signal being indicative of the absorption peak characteristic of the methyl group in the silicone coating; and a processor connected to the detector and operable to process the signal therefrom so as to substantially continuously measure the amount of silicone coating on the moving web.

11. The apparatus according to claim 10, wherein the apparatus is operable to measure the absorption peak of the silicone coating at a wavelength of about 3.4 micrometers.

12. The apparatus according to claim 10, wherein the apparatus is disposed a distance of less than 50 millimetres from the web.

13. The apparatus according to claim 10, wherein the apparatus is disposed a distance of less than 6 millimetres from the web.

\* \* \* \* \*

UNITED STATES PATENT AND TRADEMARK OFFICE
CERTIFICATE OF CORRECTION

PATENT NO.    : 6,627,043 B1
DATED         : September 30, 2003
INVENTOR(S)   : Mäntylä

It is certified that error appears in the above-identified patent and that said Letters Patent is hereby corrected as shown below:

Column 1,
Line 54, cancel "radiation", second occurrence.

Column 2,
Line 56, "Invention" should read -- invention --.

Column 5,
Line 26, cancel "oil".

Signed and Sealed this

Thirteenth Day of January, 2004

JON W. DUDAS
*Acting Director of the United States Patent and Trademark Office*